United States Patent [19]
Code

[11] Patent Number: 6,146,725
[45] Date of Patent: Nov. 14, 2000

[54] ABSORBENT COMPOSITION

[76] Inventor: Kenneth Reay Code, 6309 -187 Street, Edmonton, Alberta, Canada, T5T 2R7

[21] Appl. No.: 08/940,750

[22] Filed: Sep. 30, 1997

[30] Foreign Application Priority Data

Dec. 3, 1996 [CA] Canada .................................. 2 191 928

[51] Int. Cl.⁷ .................................. B32B 5/00; B32B 9/04
[52] U.S. Cl. ........................ 428/35.2; 428/98; 428/304.4; 428/305.5
[58] Field of Search ................. 428/35.2, 304.4, 428/305.5, 98; 442/148

[56] References Cited

U.S. PATENT DOCUMENTS

| | | | |
|---|---|---|---|
| 4,355,021 | 10/1982 | Mahl et al. ............................ | 424/28 |
| 4,363,322 | 12/1982 | Andersson ........................... | 128/290 R |
| 4,756,937 | 7/1988 | Mentezr . | |
| 5,104,660 | 4/1992 | Chvapil et al. ......................... | 424/445 |
| 5,372,766 | 12/1994 | Roe ......................................... | 264/126 |

FOREIGN PATENT DOCUMENTS 0 651 983 A1  5/1995  European Pat. Off. .

*Primary Examiner*—Richard Weisberger
*Attorney, Agent, or Firm*—Davis and Bujold

[57] ABSTRACT

An absorbent composition includes a mixture of chemicals with an absorbent that are capable of generating an antiseptic when exposed to water. The preferred form of antiseptic is Iodine, as Iodine leaves a dye marker that provides a visual indication that leakage has occurred.

8 Claims, 4 Drawing Sheets

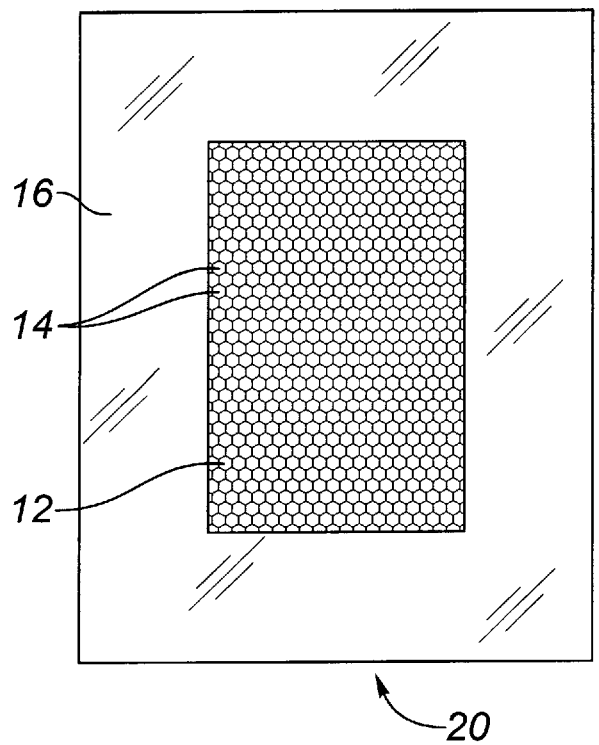
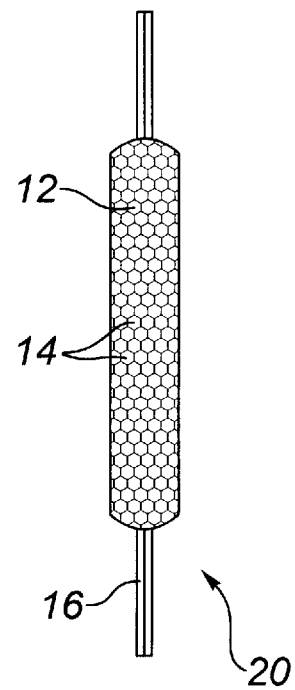
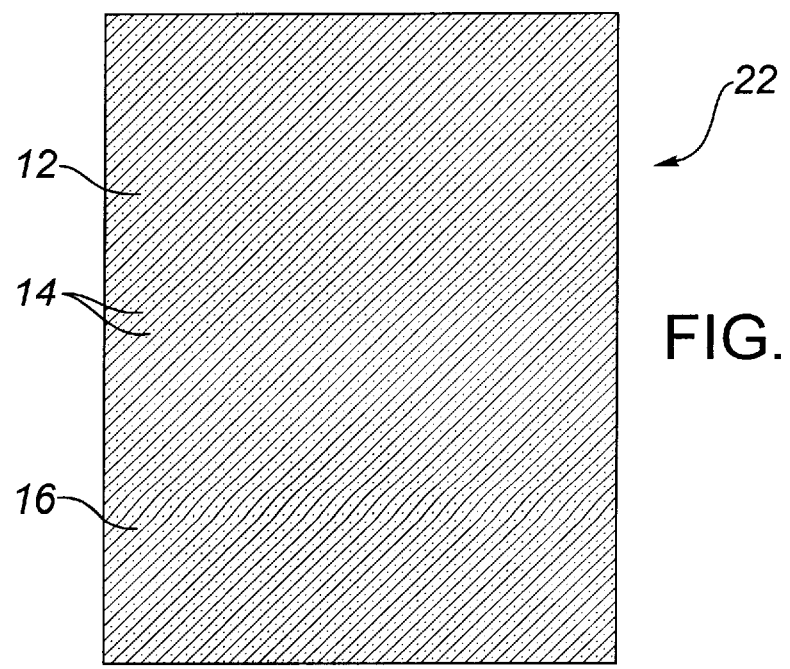

FIG. 3A
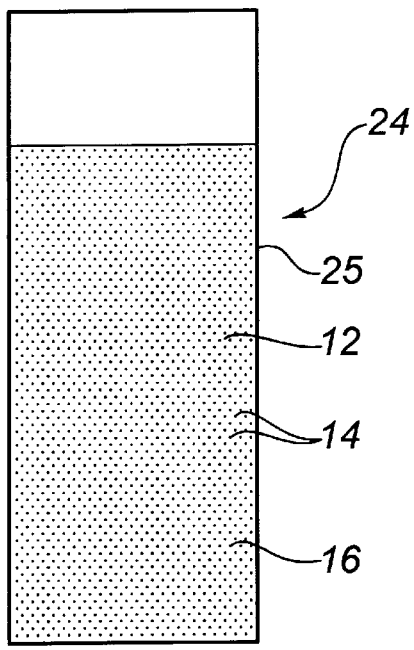
FIG. 3B
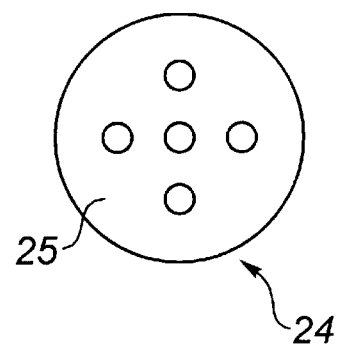
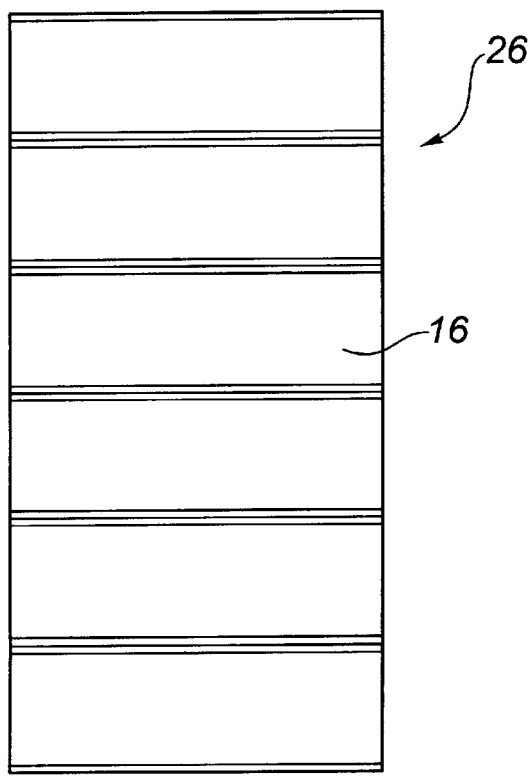
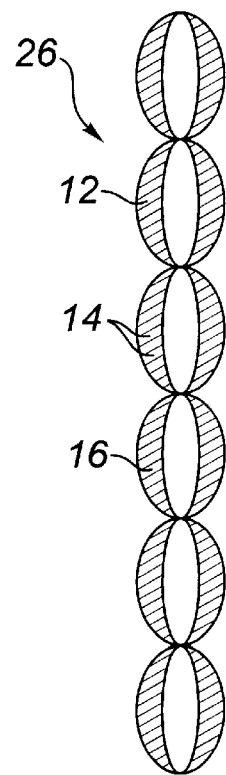
FIG. 4A
FIG. 4B

ABSORBENT COMPOSITION

FIELD OF THE INVENTION

The present invention relates to an absorbent composition and, in particular, an absorbent composition used in the transport of specimens of bodily fluids.

BACKGROUND OF THE INVENTION

An analysis of specimens of bodily fluids is extensively used in modern medicine as a diagnostic tool. Hundreds of thousands of such specimens are forwarded by air or ground transport for analysis every week. A portion of these specimens contain highly infectious diseases, and as such, present a potential hazard to those persons handling the specimens during transport. Should a transport worker become infected, there is a danger that the worker's family and other members of the public with whom the transport worker is in communication will also become infected. In recognition of the potential danger presented to the public, the member nations of the International Civil Aviation Organization (I.C.A.O.) have adopted packaging instructions for the transportation of medical, biological, and veterinary specimens. The packaging instructions require the use of a leak proof secondary container. The secondary container must have sufficient quantities of an absorbent composition to absorb the entire contents of the specimen container should a leak occur.

Although the packaging described provides a measure of protection, the use of an absorbent composition will not prevent diseases from becoming airborne. In such cases, the health of the laboratory worker is placed at risk when the secondary container is opened. The health of the transport worker is, similarly, exposed to airborne diseases should the integrity of the secondary container become compromised.

SUMMARY OF THE INVENTION

What is required is an improved form of absorbent composition that will reduce or eliminate the danger presented by airborne diseases.

According to the present invention there is provided an absorbent composition which includes an absorbent and a mixture of chemicals with the absorbent that are capable of generating an antiseptic when exposed to water.

When the above described absorbent composition is used, any leakage results in an antiseptic being generated to kill any organisms in the bodily fluids.

Although beneficial results may be obtained through the use of various absorbents, even more beneficial results may be obtained when the absorbent used is a hydrophillic resin. Hydrophillic resins are among the most efficient known absorbents.

Although beneficial results may be obtained by generating various alternative antiseptics, even more beneficial results may be obtained when the antiseptic generated is iodine. Iodine is commonly used in hospital topical antisepsis. It is also used in the production of dyes. The generation of iodine will cause discolouration within the secondary container, leaving an unmistakable visual indication that leakage has occurred.

Although beneficial results may be obtained through the use of the absorbent composition, as described above, even more beneficial results may be obtained in terms of adapting the absorbent composition to a wider range of uses when the absorbent and the mixture of chemicals are within a carrier substrate. There are a variety of carrier substrates which can be used such as a fabric, a powder, a gel, a mass of fibres, or a foam cake.

BRIEF DESCRIPTION OF THE DRAWINGS

These and other features of the invention will become more apparent from the following description in which reference is made to the appended drawings, wherein:

FIG. 1A is a top plan view of an absorbent composition in accordance with the teachings of the present invention in a fabric sack carrier substrate.

FIG. 1B is a side elevation view, in section, of the absorbent composition illustrated in FIG. 1A.

FIG. 2 is a top plan view of an absorbent composition in accordance with the teachings of the present invention in an impregnated fabric carrier substrate.

FIG. 3A is a side elevation view, in section, of an absorbent composition in accordance with the teachings of the present invention in a powder carrier substrate.

FIG. 3B is a top plan view of the absorbent composition illustrated in FIG. 3A.

FIG. 4A is a front elevation view of an absorbent composition in accordance with the teachings of the present invention in a gel carrier substrate.

FIG. 4B is a side elevation view, in section, of the absorbent composition illustrated in FIG. 4A.

DETAILED DESCRIPTION OF THE PREFERRED EMBODIMENT

Figure 5:
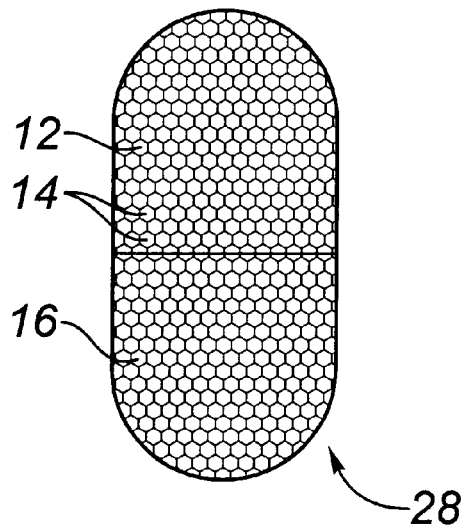
FIG. 5 is a side elevation view, in section, of an absorbent composition in accordance with the teachings of the present invention in a dissolvable gel capsule carrier substrate.

The preferred embodiment, an absorbent composition will now be described with reference to FIGS. 1A through 7B.

Referring to FIGS. 1A through 7B, each of the illustrated embodiments includes an absorbent 12 together with a mixture of chemicals 14 with absorbent 12 that are capable of generating an antiseptic when exposed to water. The various embodiments illustrated in FIGS. 1A and 7B, used different carrier substrates 16. In each case absorbent 12 has been selected to be compatible with the particular one of carrier substrates 16 used. Carrier substrates 16 are not essential, but do broaden the range of uses for the absorbent composition. The preferred form of absorbent 12 is a hydrophillic resin, due to its relatively compact size and its superior absorbent capabilities. This form of absorbent is not suited, however, for use with all carrier substrates 16. The preferred form of antiseptic is Iodine. The properties of Iodine as an antiseptic are well known, and it is already in wide spread use in hospital, laboratories and the like. Iodine has an additional desirable property in that it leaves a dye marker as a visual indication that leakage has occurred. Chemicals 14 include potassium iodine and anhydrous cupric sulfate. These chemicals are present in a stoichiometric mixture of two parts potassium iodine for every one part anhydrous cupric sulfate. When chemicals 14 are exposed to water they generate iodine.

The chemical formula relating to the reaction that occurs to generate Iodine is:

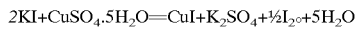

$$2KI + CuSO_4 \cdot 5H_2O = CuI + K_2SO_4 + \tfrac{1}{2}I_2 + 5H_2O$$

Referring to FIGS. 1A and 1B, in this first embodiment 20, carrier substrate 16 is a fabric sack and absorbent 12 is a polyacrylate hydrophillic resin. This form of carrier substrate is suitable for use as a companion enclosure in secondary containers specified for the transportation or storage of medical and diagnostic specimens. Beneficial results have been obtained through the use of porous papers, tea-bags, synthetic fabrics, and water soluble films which could be bonded or sewn together.

Referring to FIG. 2, in this second embodiment 22, carrier substrate 16 a fabric impregnated absorbent 12, and absorbent 12 is a powder form sodium alginate. Beneficial results have been obtained through the use of polyester fiberfills of several densities and quiltings. The polyester was selected in view of its dryness, availability, and absorbent characteristics. In tests it was determined that blood would traverse a significant distance before clotting. This form of carrier substrate is suitable for use in wrapping or taping containers on their exterior. This provides an absorptive and cushioning surface.

Referring to FIGS. 3A and 3B, in this third embodiment 24, carrier substrate 16 is an inert powder contained within a shaker 25 mixed with absorbent 12, also in powder form. The absorbent powder is sodium alginate. The ingredients are mixed, pulverized, and passed through a screen to ensure relatively uniform sizes of granules. This form of carrier substrate is suitable for use as a spill responsive surface absorber. It can also be used as a doping agent for the polyester fabric described above.

Referring to FIGS. 4A and 4B, in this fourth embodiment 26, carrier substrate 16 is a gel into which absorbent 12 is mixed. The absorbent is a polyacrylate hydrophillic resin. The gel itself is compounded as a supersaturation of gelling agent. It is supplied in film pouches including reactive constituents of the anti-infective generator. This form of carrier substrate is suitable for use in transporting frozen specimens. The thawing of the gel delays the thawing of the specimen. With radioactive specimens, the gel may contain radio-opacifyers. It should be noted, however, that the addition of heavy metal (polyvalent ions) makes necessary a significant increase in gelling agent in order to produce the gel.

Referring to FIG. 5, in this fifth embodiment 28, carrier substrate 16 is a dissolvable gel capsule having absorbent 12. A granular preparation of the absorbent composition is placed in a water soluble gelatin package in capsular or cubical form. The preferred powder absorbent is sodium alginate. This form of carrier substrate is suitable for use as a companion enclosure to secondary containers specified for the transportation or storage of medical and diagnostic specimens.

Figure 6:
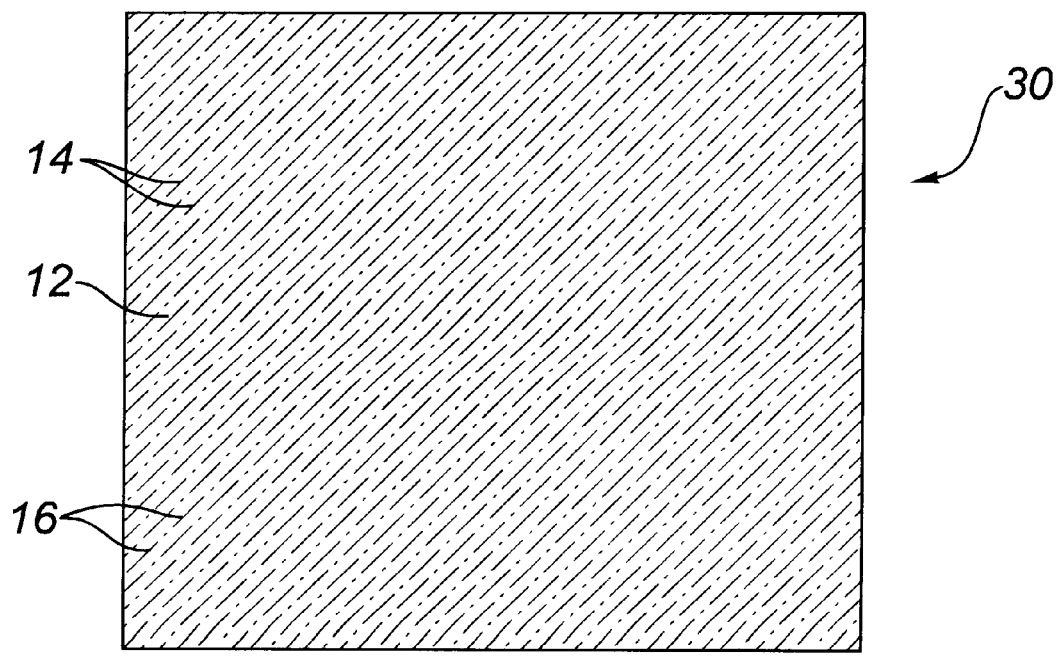
FIG. 6 is a top plan view, in section, of an absorbent composition in accordance with the teachings of the present invention in a mass of fibre carrier substrate.

Referring to FIG. 6, in this sixth embodiment 30, carrier substrate 16 is a mass of cellulose fibres intermixed with peat moss 31 containing absorbent 12. The form of absorbent 12 is sodium alginate. This form of carrier substrate is suitable for use as stuff packing or loose fill. Peat moss 31 must be subjected to significant prior oven drying in order to render it suitable for use.

Figure 7A:
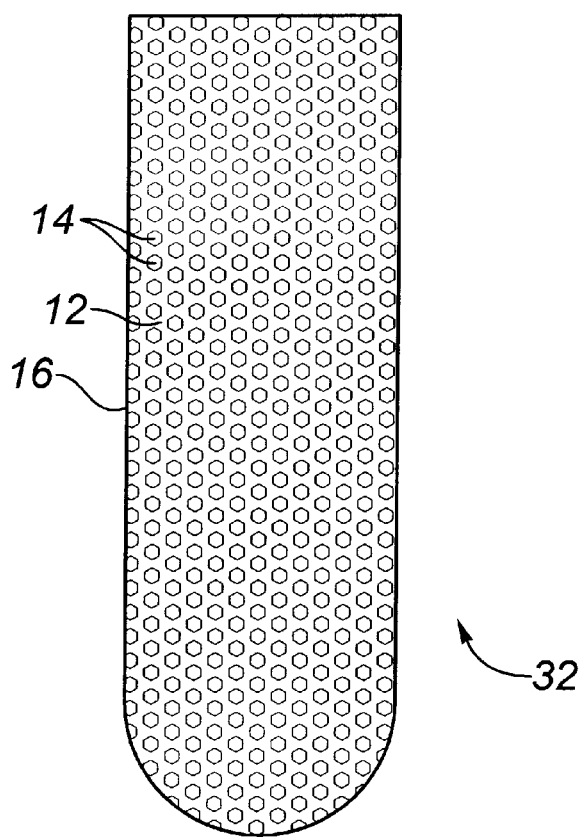
FIG. 7A is a side elevation view, in section, of an absorbent composition in accordance with the teachings of the present invention in a foam cake carrier substrate.
Figure 7B:
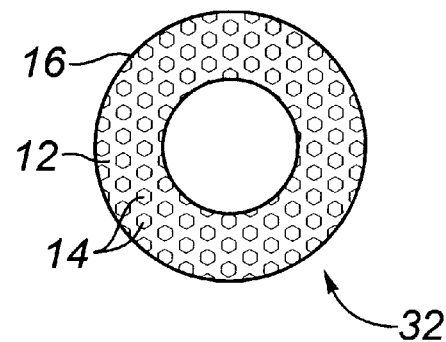
FIG. 7B is a top plan view of the absorbent composition illustrated in FIG. 7A.

Referring to FIGS. 7A and 7B, in this seventh embodiment 32, carrier substrate 16 is a foam cake containing absorbent 12. Beneficial results have been obtained through the use of polyurethane or extruded polystyrene products. Polyurethane is preferred due to its low moisture content. The best mode of retaining the constituents in preactive form is by making foams by lyophilization of gels in toluene and freeze-drying. The foam cakes are then tumbled in an absorbent of powder form sodium alginate. This form of carrier substrate is suitable for use as a molded foam carrier or as a cushioning device for a container.

The following cautionary note is included to ensure full and complete disclosure of the invention. There are various forms of copper sulfate, however, only anhydrous cupric sulfate is suitable for the present invention. The pentahydrate form initiates the evolution of iodine irreversibly upon contact with the potassium iodine. In selecting a carrier substrate care must be taken as to the water content of the substrate, as the presence of water initiates the reaction. One experimenting with this art must be prepared for iodine gas, and have regard to the Material Safety Data Sheet relating to Iodine. Iodine stains may be removed with solutions of sodium thiosulfate or ammoniated alcohol.

It will be apparent to one skilled in the art that modifications may be made to the illustrated embodiment without departing from the spirit and scope of the invention as hereinafter defined in the Claims.

What is claimed is:

1. An absorbent composition, comprising:
   a carrier substrate;
   a hydrophillic resin in the carrier substrate;
   a mixture of chemicals within the carrier substrate that are capable of generating iodine when exposed to water, the mixture of chemicals including potassium iodine and cupric sulfate.

2. The absorbent composition as defined in claim 1, wherein the mixture of chemicals includes potassium iodine and anhydrous cupric sulfate in a stoichiometric mixture of two parts potassium iodine for every one part anhydrous cupric sulfate.

3. The absorbent composition as defined in claim 1, wherein the hydrophillic resin is polyacrylate.

4. The absorbent composition as defined in claim 1, wherein the carrier substrate is a fabric sack.

5. The absorbent composition as defined in claim 1, wherein the carrier substrate is a mass of fibres.

6. The absorbent composition as defined in claim 5, wherein the mass of fibres are cellulose.

7. The absorbent composition as defined in claim 5, wherein the mass of fibres include peat moss.

8. The absorbent composition as defined in claim 1, wherein the carrier substrate is a foam cake.

* * * * *